United States Patent
Ding

[11] Patent Number: 5,899,935
[45] Date of Patent: May 4, 1999

[54] BALLOON EXPANDABLE BRAIDED STENT WITH RESTRAINT

[75] Inventor: Ni Ding, Plymouth, Minn.

[73] Assignee: Schneider (USA) Inc., Minneapolis, Minn.

[21] Appl. No.: 08/905,704

[22] Filed: Aug. 4, 1997

[51] Int. Cl.$^6$ .................................. A61F 2/06; A61F 2/04
[52] U.S. Cl. ................................................. 623/1; 623/12
[58] Field of Search .................................. 623/1, 11, 12; 606/191, 194, 195, 198

[56] References Cited

U.S. PATENT DOCUMENTS

| | | |
|---|---|---|
| 4,655,771 | 4/1987 | Wallsten . |
| 4,733,665 | 3/1988 | Palmaz . |
| 5,026,377 | 6/1991 | Burton et al. . |
| 5,234,456 | 8/1993 | Silvestrini ............................... 606/194 |
| 5,304,121 | 4/1994 | Sahatjian ................................. 606/194 |
| 5,464,650 | 11/1995 | Berg et al. . |
| 5,545,208 | 8/1996 | Wolff et al. ............................... 623/12 |
| 5,575,818 | 11/1996 | Pinchuk .................................... 623/12 |
| 5,591,222 | 1/1997 | Susawa et al. . |
| 5,591,224 | 1/1997 | Schwartz et al. . |
| 5,632,772 | 5/1997 | Alcime et al. ............................. 623/12 |
| 5,725,567 | 3/1998 | Wolff et al. ................................. 623/1 |

FOREIGN PATENT DOCUMENTS 709068  5/1996  European Pat. Off. .

Primary Examiner—David J. Isabella
Assistant Examiner—John M. Black
Attorney, Agent, or Firm—Nikolai, Mersereau & Dietz, P.A.

[57] ABSTRACT

A method of making a balloon expandable braided stent with a restraint to initially prevent self-expansion and the resulting product. Multiple strands of a resilient metal or plastic are braided to form a tubular configuration of a predetermined outside diameter which assumes a lesser diameter when the tubular stent is longitudinally stretched. When in its stretched condition, it is coated with a polymeric material which is then cross-linked to effectively "freeze" the intersections of the braided structure holding it in its reduced diameter configuration. The tubular stent is designed to be placed within a body vessel using a balloon stent delivery catheter. When the balloon surrounded by the braided wire stent is inflated, the stent expands initially to an extent to break the bonds of plastic material between the intersections of the strands, thereby permitting self-expansion to take place. The coating may also comprise a hydrogel or an elastomeric impregnated with the water soluble particles which softens and/or deteriorates upon exposure to an aqueous media, such as blood.

11 Claims, 4 Drawing Sheets

```
┌─────────────────────────────────────┐
│   BRAID RIGID BUT FLEXIBLE STRANDS  │
│      AND HEAT TREAT ON A MANDREL    │
│   TO FORM A SELF-EXPANDING TUBULAR  │
│    BODY STRUCTURE OF A FIRST PRE-   │
│            DETERMINED O. D.         │
└─────────────────────────────────────┘
                   │
                   ▼
┌─────────────────────────────────────┐
│  LONGITUDINALLY STRETCH THE TUBULAR │
│  BODY STRUCTURE TO REDUCE THE O.D. TO│
│    A SECOND PREDETERMINED VALUE     │
└─────────────────────────────────────┘
                   │
                   ▼
┌─────────────────────────────────────┐
│    COAT THE STRETCHED TUBULAR BODY  │
│  STRUCTURE WITH A POLYMERIC RESTRAINT│
│       TO "FREEZE" THE O.D. OF THE   │
│      TUBULAR BODY STRUCTURE AT OR   │
│     NEAR THE SECOND PREDETERMINED   │
│                 VALUE               │
└─────────────────────────────────────┘
```

*FIG. 4*

BALLOON EXPANDABLE BRAIDED STENT WITH RESTRAINT

BACKGROUND OF THE INVENTION

I. Field of the Invention

This invention relates generally to the manufacture of vascular stents, and more particularly to a method of making an otherwise self-expanding stent balloon expandable.

II. Discussion of the Prior Art

Various types of stents are described in the prior art and they generally fall into one of two classes, namely, self-expanding stents and balloon expandable stents. A common type of self-expanding stent is referred to as a "Wallstent® Endoprosthesis" and is described in U.S. Pat. No. 4,655,771 to Wallsten, which is incorporated herein by reference in its entirety. It comprises a braided tubular structure of metal wires or monofilament plastic strands. The tubular structure is characterized by a longitudinal shortening upon radial expansion.

In use, such a stent may be longitudinally extended to achieve a reduced radial diameter and placed within the lumen of a delivery catheter. The delivery catheter may then be advanced through the vascular system until its distal end is located proximate a stenotic lesion to be stented. The stent is then deployed out the distal end of the catheter and when unconstrained by the catheter, it self-expands into contact with the vessel with sufficient radial force so that it is maintained in the blood vessel for an extended period of time. A suitable delivery device for a Wallstent® Endoprosthesis is shown in U.S. Pat. No. 5,026,377 to Burton et al.

An example of a balloon expandable stent is the "Palmaz™" balloon expandable stent described in U.S. Pat. No. 4,733,665. A balloon expandable stent may comprise a fenestrated tube of material having a low modulus of elasticity and with substantially no memory property. The fenestrations through the wall of the tube are such that when the tube is placed over the deflated balloon on a balloon delivery catheter and then is routed to the location in the vascular system where it is to be used, the inflation of the balloon deforms the stent from a reduced diameter to a larger operating diameter. The balloon is then deflated and withdrawn, leaving the stent in place.

A need exists for a stent that has the self-expanding characteristics of a braided stent, but which can be delivered over a balloon for accurate positioning and deployment. The present invention fulfills that need.

SUMMARY OF THE INVENTION

The method of the present invention provides a balloon expandable stent that comprises a tube of braided wire having a relatively small outside diameter when in a longitudinally extended state and which normally self-expands to a larger outside diameter when in a longitudinally contracted state. As used herein, the "free state" of a self-expanding stent is the state that is reached when no external forces are applied thereto. This free states corresponds to a radially fully expanded state. The braided tube is coated with either a brittle material or a material that will readily soften when exposed to body fluids for initially restraining the braided wire tube from self-expanding to the larger outside diameter when external forces are removed. When the coated braided wire tube is concentrically disposed over the balloon of a stent delivery catheter and the balloon is inflated, the restraining force imposed by the brittle coating is effectively broken, allowing the device to self-expand.

It has also been found expedient to incorporate into the coating of the polymeric material an effective amount of water-soluble solid particles that, when dry act to reinforce the coating, and when placed in an aqueous medium, such as blood, will elute with time and thereby lessen the restraint imparted by the coating on the intersections of the wires comprising the braided wire tube, permitting expansion thereof. The particles may comprise a drug.

The method of manufacturing the balloon expandable stent comprises the steps of first braiding a plurality of resilient metal or plastic strands having a memory property into a tubular structure of a predetermined outer diameter. Then the resulting tubular structure is heat treated on a mandrel at a suitable temperature to cause stress relief (generally about 500–600° C. (For Elgiloy®) thereby causing the tubular structure to conform to the shape of the mandrel. Next, the tubular structure is stretched longitudinally to reduce its outer diameter and, while it is clamped and held in the stretched condition, the tubular structure is coated or otherwise treated with a brittle plastic or other material capable of freezing the intersections against movement. If a cross-linkable material containing a water soluble powder is to be used, the material is cross-linked either by application of heat and/or radiation, such that the coating holds the stent in its stretched state and precludes self-expansion thereof to its predetermined outer diameter, even when the force used to longitudinally stretch the tubular structure is removed. When used, the tubular structure may be concentrically positioned over an uninflated balloon on a balloon delivery catheter and, following the passage of the balloon and stent through the vascular system to the site of a lesion, the balloon is inflated to radially expand the tubular structure sufficient to rupture or disintegrate the coating and allow self-expansion of the tubular structure. The destruction of the integrity of the coating is achieved by the use of a hydrogel as the coating or the inclusion of soluble particles in the polymeric matrix and the subsequent exposure of the coated device to an aqueous medium.

DESCRIPTION OF THE DRAWINGS

FIG. 4 is a flow chart illustrating the steps involved in one method of making a balloon expandable braided stent incorporating a polymeric restraint.

DESCRIPTION OF THE PREFERRED EMBODIMENT

Figure 1:
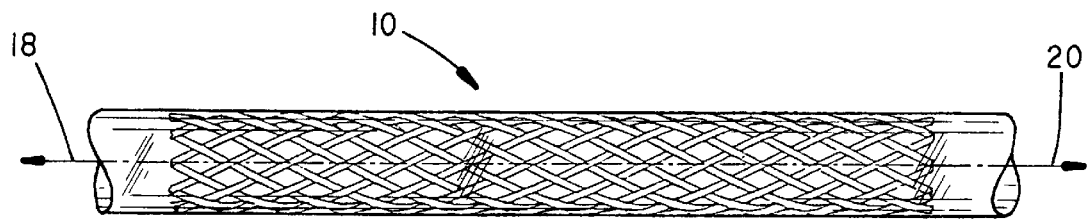
FIG. 1 is an enlarged side elevational view of a self-expanding stent that has been treated with a material in accordance with the method of the present invention to lock the intersections of longitudinally stretched stent.
Figure 2:
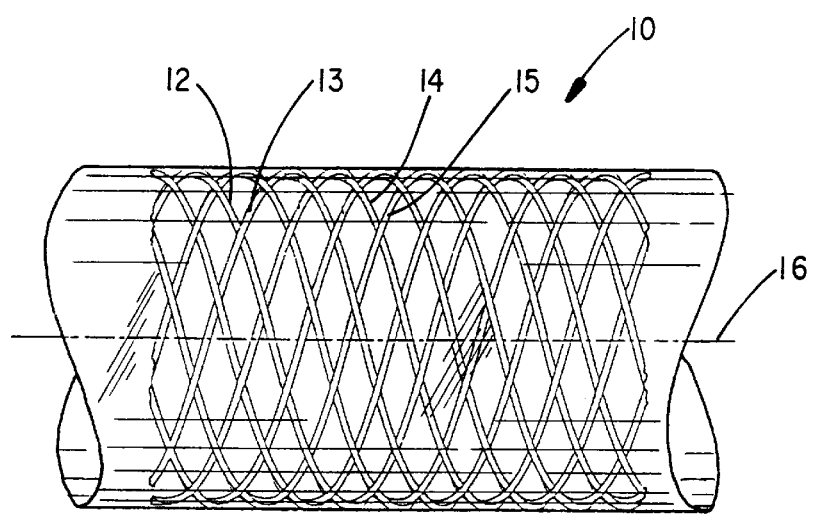
FIG. 2 illustrates the stent of FIG. 1 after it has been balloon expanded.
Figure 3:
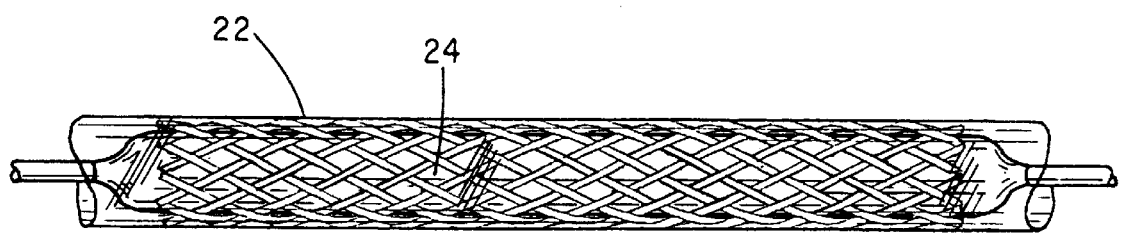
FIG. 3 is a drawing showing a coated stent surrounding an uninflated balloon on a delivery catheter and contained within a protective, moisture impervious sheath.

Referring to FIGS. 1 and 2, the balloon expandable braided stent constructed in accordance with the present invention is indicated generally by numeral 10 and is seen to comprise a plurality of rigid, but flexible strands 12, 13, 14 and 15, each of which extends in a helix configuration with the center line of the resulting tubular body as a common axis 16. A first group of strands are wound in the same direction, but are axially displaced relative to one another. These strands cross with another set of strands that are also axially displaced with respect to one another, but which have the opposite winding direction.

The braiding machine used to interweave the strands may be controlled so as to include a sufficient number of strands in the braid as well as a pick to provide a stable configuration corresponding with the outside diameter (O.D.) of the stent body when it is unconstrained (free state), as well as the angle of intersection of the crossing strands. The strands themselves may be metal, such as stainless steel, a nickel-titanium alloy or clad composite construction as shown in U.S. Pat. No. 5,628,787 to Mayer or, alternatively, may be a suitable medical grade plastic monofilament.

The braided structure is such that the application of a longitudinal stretching force, such as represented by the force vectors 18 and 20 in FIG. 1, results in an elongation of the stent body and a corresponding reduction in its radial dimension. The device is self-expanding in that when the longitudinal stretching forces are relieved, the tubular body will diminish in length while expanding radially.

A conventional self-expanding braided stent of the type heretofore described may be implanted within a tubular body vessel, such as an artery, by first radially compressing it so as to reduce its diameter to the point where the stent can be inserted into the lumen of a stent delivery catheter. The delivery catheter containing the stent may then be routed through the vascular system until the distal end thereof is disposed proximate the site of a lesion or the like to be bridged. An outer sleeve is then withdrawn to expel the compressed stent from the distal end of the delivery catheter and when no longer constrained by the delivery catheter, the stent will self-expand, radially, to present a significantly larger outside diameter selected so that it will continue to press itself against the interior wall of the blood vessel in question.

The flow chart of FIG. 4 shows an example of the steps involved in making the stent of the present invention. To render the braided stent of the present invention balloon expandable and, therefore, easier to position, the woven stent, after it comes off the braiding machine and is heat treated, is then clamped at opposite ends and longitudinally stretched as illustrated in FIG. 1. While in this stretched condition, the stent is dipped in or sprayed with a solution of a suitable polymer in a volatile solvent, spot glued with such a solution or a melt polymer, and then air dried or heated to drive off the solvent and to cure the polymer to effectively "freeze" the stent in its elongated, reduced diameter configuration even when the stretching forces represented by the vectors 18 and 20 are removed. The cured polymeric coating creates a restraint between the opposed sets of helical windings at their points of intersection and prevents self-expansion from taking place. Suitable polymers for this method include hydrogel materials.

An alternative method for making the device includes, while the stent is in the stretched condition, applying a brittle polymer or inorganic material to the stent by vapor deposition or ion beam assisted deposition. Suitable materials for vapor deposition include parylene and pyrolytic carbon which are quite brittle. A suitable material for ion beam assisted deposition includes ceramic coatings which are also quite brittle.

It is further contemplated that a water-soluble powder be blended with an elastomer, such as silicone, which serves as a reinforcer when the coating is dry. When the coated stent is exposed to blood, the powder particles will dissolve, weakening the coating's restraining effect on the elongated, radially reduced stent, thus facilitating its ability to later self-expand. Further, the powder may comprise an anti-platelet agent, an anti-coagulant agent, an anti-microbial agent, an anti-proliferative agent, an anti-metabolic agent and an anti-inflammatory agent, a drug for enhancing endothelial growth for holding the stent in place or for inhibiting thrombosis. When dry, the drug or water-soluble powder particles reinforce the coating. Upon contact with an aqueous media, the drug or water soluble component (e.g. salt, sugar, drug, etc.) will elute from the matrix and gradually soften the coating and allow later self-expansion of the stent.

A cross-linkable system can also be applied as a polymeric restraint. In this case, the coating can be applied while the stent is in its free state. Thereafter, the coated stent is longitudinally stretched to a reduced diameter and then cross-linked to restrain the opposed sets of helical windings at their points of intersection.

Figure 5:
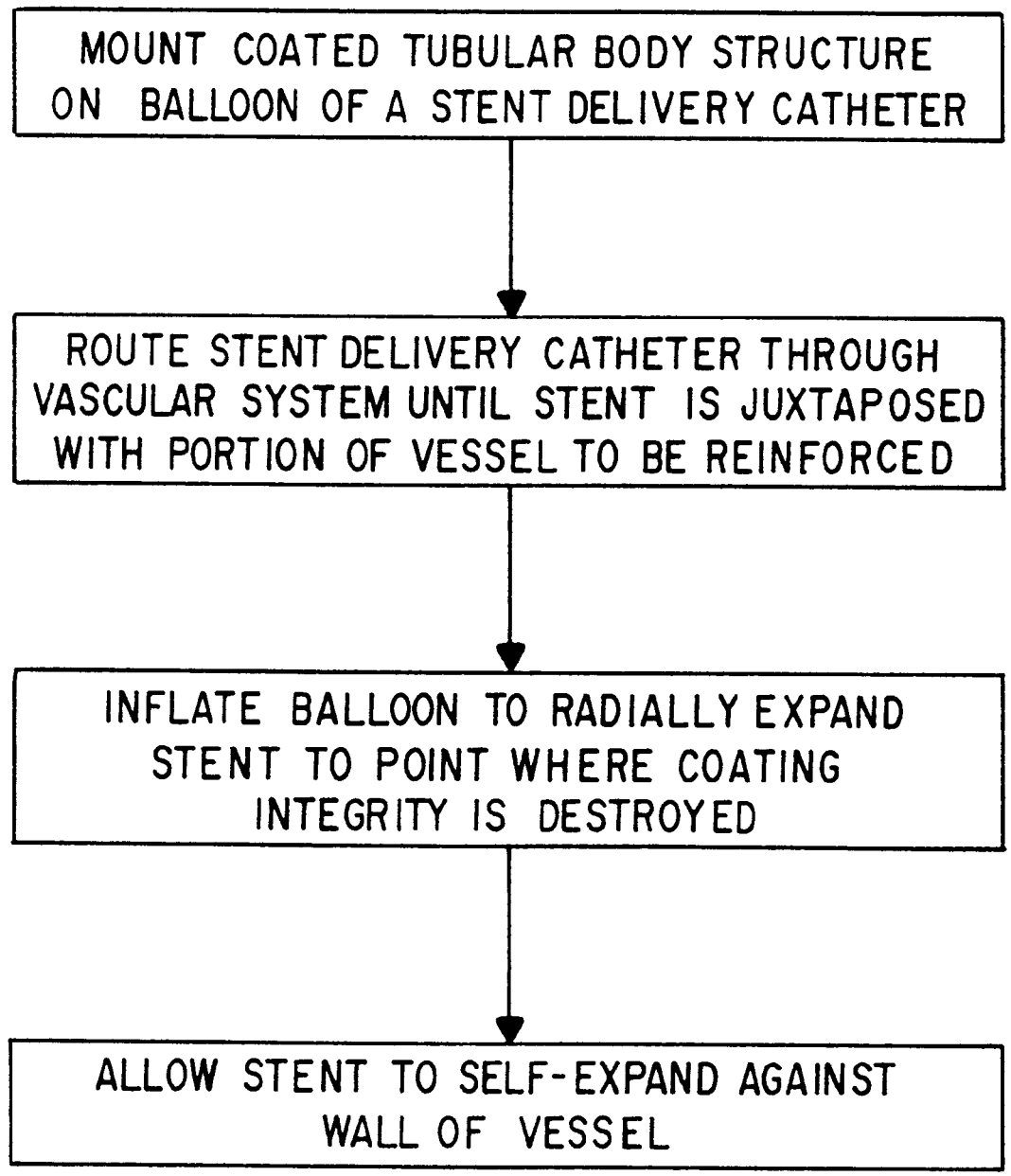
FIG. 5 is a flow chart of the steps involved in using the balloon expandable self-expanding stent of the present invention.

FIG. 5 is a flow chart showing an example of the steps involved in using the improved stent. Rather than deploying the stent of the present invention solely by allowing self-expansion from the lumen of a delivery catheter, the device of the present invention may be placed over an uninflated balloon on a balloon-type stent delivery catheter. With the stent so mounted, the catheter may be routed through the vascular system until the stent is juxtaposed to the site where reinforcement is desired. Now, as inflation of the balloon takes place and the stent begins to expand, the brittle coating bonding the stent strand intersections are broken and the stent is allowed to self-expand to the point where it presses against the vessel wall with a force sufficient to maintain the stent in place following deflation of the delivery balloon and removal of the catheter.

To prevent premature self-expansion of the stent when coated with a powder impregnated polymer or hydrogel as it is being advanced through the vascular system, it may be contained within a moisture impermeable sheath 22 as shown in FIG. 6. This protective sheath prevents the stent from coming into contact with water (blood) before the deployment. Immediately after the withdrawal of the sheath, the balloon is inflated, breaking some of the restrained points or realigning the polymer chain to facilitate the water coming in and the drug or other soluble powder component eluting out, allowing the stent to assume the profile which the balloon creates. Since a typical balloon inflation time is 30 seconds or more, the coating is further softened during the inflation operation, and the stent will eventually fully open and recover its inherent property. Experiments have shown that even without balloon expansion, the treated stent will recover by itself as the polymer matrix loses structural integrity due to the dissolving powders.

Depending on the amount of the drug or other powder embedded, the solubility of the drug or other powders and the cross-linked density of the coating, the elution rate, and hence the softening speed, can be adjusted. My experiments have shown that the coating can be applied on the stent, either at a constrained stage or a free stage, stretched while curing and the coated stent will maintain its tubular constrained shape, after the coating is fully cured.

EXAMPLE

The typical procedure for the stretching cure of soluble powder impregnated silicone is as follows: A self-expandable Wallstent® Endoprosthesis having a nominal (free state) diameter of 4 mm is coated with a 37.5 percent heparin in silicone suspension and then stretched longitudinally in a clamping fixture and heat-cured in a convection oven at a temperature of about 90° C. for a time period of 16 hours. The stent is then inserted into a small diameter nylon sheath and further cured during a gamma sterilization process at a dosage of 2.5–3.5 mrad. When extracting the coated stent from the nylon sheath, the stent was found to remain constrained. In its constrained state, it was then mounted on a 3.5 mm balloon catheter. When emersed in water and inflated, the stent was found to recover 90% or more of its nominal diameter within about 30 seconds and eventually fully opened.

While heparin impregnated silicone coating is preferable, other cross-linkable polymers that may be employed in practicing the invention include cross-linkable polyurethane, cellulose, fluoropolymers, polyolefins, diene polymers and unsaturated polyesters.

The longitudinally stretched, self-expanding wall stent may also be treated with a hydrogel material to temporarily maintain the stent in its stretched state prior to implantation. When the hydrogel is dry, it behaves like the previously mentioned hard or brittle plastic. When exposed to an aqueous media, it will promptly penetrate into the hydrogel to swell the material and soften the coating. The mechanical property of the self-expanding stent will then again dominate. Thus, a protective sheath is again required during the implantation of the hydrogel coated stent. Typical examples of hydrogel materials useful in the practice of the present invention are polyvinyl alcohol, polyvinyl acetate, polyvinylpyrrolidone, polyacrylamide, polyacrylic acid, polyhydroxyethyl methacrylate, polyethylene oxide, polyglycolic acid (PGA), polylactic acid (PLA), and PGA-PLA copolymers.

What is claimed is:

1. A balloon expandable stent comprising:
   (a) a tube of braided strands having a relatively small outside diameter when stretched longitudinally and which normally self-expands to a larger outside diameter when in a free state; and
   (b) a coating of a material on at least portions of some of the strands for initially restraining the braided strand tube from self-expanding to the larger outside diameter when in the free state.

2. The balloon expandable stent as in claim 1 the coating is a frangible material.

3. The balloon expandable stent as in claim 2 the frangible material is ceramic.

4. The balloon expandable stent as in claim 2 wherein the frangible material is a polymer.

5. The balloon expandable stent as in claim 4 wherein the polymer is selected from the group consisting of paralyne and pyrolitic carbon.

6. The balloon expandable stent as in claim 1 the coating material is a hydrogel.

7. The balloon expandable stent as in claim 6 wherein the hydrogel is selected from the group consisting of polyvinyl alcohol, polyvinyl acetate, polyvinylpyrrolidone, polyacrylamide, polyacrylic acid, polyhydroxyethyl methacrylate, polyethylene oxide, polyglycolic acid (PGA), polylactic acid (PLA), and PGA-PLA copolymers.

8. The balloon expandable stent as in claim 1 wherein the strands comprise a resilient metal wire.

9. The balloon expandable stent as in claim 1 wherein the strands comprise a monofilament of a polymeric material.

10. The balloon expandable stent as in claim 1 the coating material comprises a polymer which initially contains an effective amount of water soluble solid particles that when placed in an aqueous medium elute and thereby lessen the restraint by the coating on the braided tube permitting self-expansion thereof.

11. The balloon expandable stent as in claim 10 wherein the polymer is an elastomeric polymer selected from the group consisting of silicone, polyurethane, cellulose, fluoropolymers, polyolefins, diene polymers, and unsaturated polyesters.

* * * * *